July 29, 1958 W. G. McLELLAN, JR Plant Pat. 1,734
CARNATION
Filed July 30, 1957
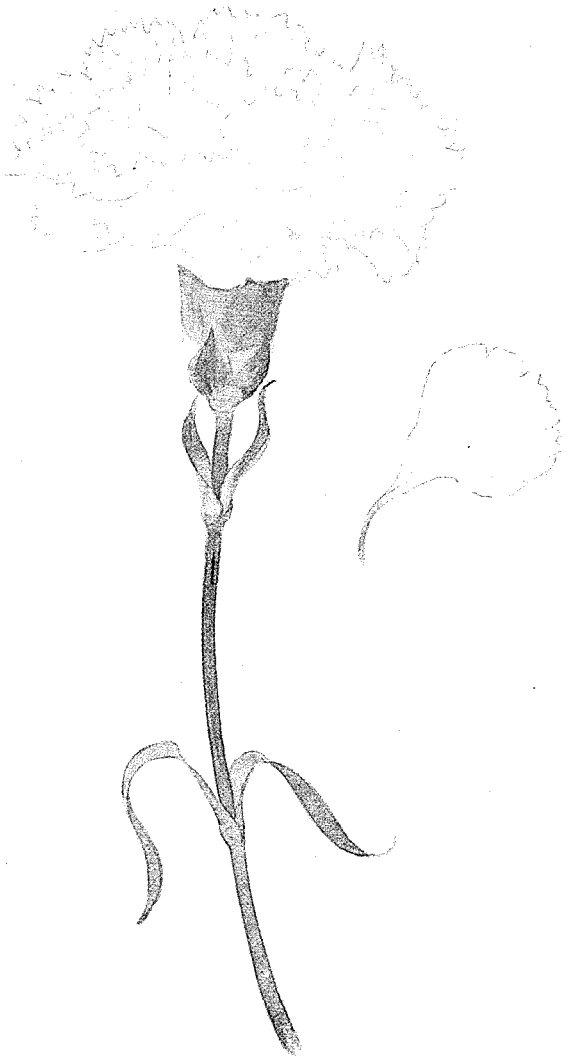
INVENTOR.
WAKEMAN G. McLELLAN JR.
BY
Boykin, Mohler & Wood
ATTORNEYS United States Patent Office Plant Pat. 1,734
Patented July 29, 1958

1,734

CARNATION

Wakeman G. McLellan, Jr., Atherton, Calif., assignor to E. W. McLellan Company, Mount Eden, Calif., a corporation of California Application July 30, 1957, Serial No. 675,236

1 Claim. (Cl. 47—60)

This invention relates to improvements in carnations and the object of the invention is to provide a new and distinct variety of carnation plant in which the blossom is of a distinctive color not previously existing in any known variety.

This new variety is from a sport from the Harvest Moon plant that normally produces a yellowish gold colored blossom, the parent of which is the Sim variety of carnation. There is no record of a patent covering the Harvest Moon plant, which plant was registered as a new variety on August 16, 1951, with the American Carnation Society, New Augusta, Indiana.

Asexual propagation of the newly discovered plant was made at Mount Eden, California, by taking cuttings in the years 1955, 1956 and 1957 and growing them.

The cuttings so taken and grown have consistently produced blossoms having the new and distinctive color hereinafter described more in detail.

The accompanying illustration shows a blossom on a stalk, and a petal taken from the blossom.

The following is a detailed description of the new carnation.

As above noted, the newly discovered variety is from a sport taken from a Harvest Moon plant, the parent of which is the Sim variety of carnation that is shown and described in United States Letters Plant Patent No. 669, issued January 15, 1946, to W. Sim. The Harvest Moon carnation plant variety is identical to the William Sim carnation plant variety except for color.

The description of the carnation in the above designated patent is applicable to the newly discovered variety; with one exception, namely: the color of the blossom.

The petals of the blossom are substantially uniform in color, which may be of a slightly lighter shade at the base where not fully exposed to light, and which color relatively closely approximates the color designated "Coral Blush" shown in Plate I, row 10, column F, in the Dictionary of Color, by A. Maerz and M. Rea Paul, published in 1930 by McGraw-Hill Book Company, Inc., New York city, New York. Slight variations in the tint or shade may occur but the color remains substantially uniform and the range of tint variation may come substantially within the variations shown in Plate I, rows 10, 11, columns C to G in said publication.

I claim:

The new and distinct variety of carnation plant substantially as herein described and illustrated.

No references cited.